United States Patent
Karabutov et al.

(10) Patent No.: US 8,368,289 B2
(45) Date of Patent: Feb. 5, 2013

(54) NONDESTRUCTIVE TESTING APPARATUS AND METHOD

(75) Inventors: Alexander Karabutov, Moscow (RU); Mikhail Lyamshev, Moscow (RU); Vladislav Mikhalevich, Moscow (RU); Manomohan Subudhl, East Setauket, NY (US); Upendra Rohatgl, East Setauket, NY (US)

(73) Assignee: SpectraQuest, Inc., Richmond, VA (US)

( * ) Notice: Subject to any disclaimer, the term of this patent is extended or adjusted under 35 U.S.C. 154(b) by 0 days.

(21) Appl. No.: 12/993,597

(22) PCT Filed: Apr. 10, 2009

(86) PCT No.: PCT/US2009/040206
§ 371 (c)(1), (2), (4) Date: Apr. 6, 2011

(87) PCT Pub. No.: WO2009/126886
PCT Pub. Date: Oct. 15, 2009

(65) Prior Publication Data
US 2011/0187233 A1    Aug. 4, 2011

(30) Foreign Application Priority Data
Apr. 10, 2008   (RU) ................................ 2008113451

(51) Int. Cl.
H01L 41/08    (2006.01)
(52) U.S. Cl. ........................................ 310/336; 310/311
(58) Field of Classification Search .................. None
See application file for complete search history.

(56) References Cited

U.S. PATENT DOCUMENTS

| | | | |
|---|---|---|---|
| 4,541,280 A | 9/1985 | Cielo et al. | |
| 5,557,156 A * | 9/1996 | Elings | 310/316.01 |
| 5,767,408 A * | 6/1998 | Lindgren et al. | 73/597 |
| 5,781,304 A | 7/1998 | Kotidis et al. | |
| 6,945,114 B2 * | 9/2005 | Kenderian et al. | 73/643 |
| 7,383,732 B2 * | 6/2008 | Okumura et al. | 73/602 |
| 7,395,827 B2 * | 7/2008 | Madanshetty | 134/184 |
| 7,573,177 B2 * | 8/2009 | Fuller et al. | 310/311 |

OTHER PUBLICATIONS

Ivochkin, et al., Application of laser generated ultrasonic pulses in diagnostics of residual stresses in welds, Proc. of SPIE vol. 6053, Jun. 2006.

Ivochkin, et al., Measurement of Velocity Distribution for Longitudinal Acoustic Waves in Welds by a Laser Optoacoustic Technique, ISSN 1063-7710, Acoustical Physics, 2007, vol. 53, pp. 471-477, Pleides Publishing Ltd. 2007.

* cited by examiner

Primary Examiner — Mark Budd
(74) Attorney, Agent, or Firm — Bernard G. Pike; Pike IP Law, PLLC

(57) ABSTRACT

A laser opto-acoustic apparatus and method is applied for nondestructive testing of defects and residual stresses in solids. A nondestructive testing apparatus may have a piezoelectric transducer for measuring oscillations in a solid. The oscillations or waves may be caused from longitudinal, shear, and/or Raleigh waves in the object to be tested. The nondestructive testing apparatus may also include a laser. The laser is capable of generating the longitudinal, shear, and/or Raleigh waves in the object. One method of performing nondestructive testing of materials may include creating at least one of a longitudinal, shear, and/or Raleigh wave in an object and measuring the speed of the wave in the object. The speed of the waves may be compared with the speed of waves in a material without defects to determine whether the object to be tested has defects.

16 Claims, 9 Drawing Sheets

NONDESTRUCTIVE TESTING APPARATUS AND METHOD

FIELD OF THE INVENTION

The invention relates to the field of nondestructive testing. In certain embodiments, the nondestructive testing apparatus comprises a laser and a piezoelectric transducer. In certain embodiments, the nondestructive testing apparatus may be capable of measuring defects such as residual stress in solids. One method of performing nondestructive testing of materials may comprise creating a surface acoustic wave on a material and measuring the speed of the surface acoustic wave on the surface of the material.

BACKGROUND

Defects in metallic structures may reduce the service life of a machine part, structural component, pipe, turbine, or other component. Defects may include residual stresses, delamination, porosity, cracks, microcracks or other features in a material due to a manufacturing process such as heat treatment, cooling, annealing, forming, impurities, or welding. Any of these defects may be sites for initiation or propagation of cracks, for example. The cracks may lead to weakening and eventual failure of the material.

Methods for nondestructive testing of materials have been developed. The method of testing the welded structure or other machine part depends on the application that the part will be used. A weld for structural component may not be required to be as high a welding standard as a weld for pipe containing a hazardous component. Therefore, appropriate testing methods can assure a weld meets applicable standards. Currently, there are a variety of nondestructive testing methods including visual, dye penetrant, magnetic particle, ultrasonic and X-ray methods.

Visual Inspection

Visual inspection is often the most cost-effective method and is conducted during and after welding, but is the least reliable method. Visual inspection requires little equipment and involves prewelding visual inspection of the materials, confirmation of the correct welding equipment and material, and a visual inspection after each welding pass. During fabrication, visual examination of a weld bead and the end crater may reveal problems such as cracks, inadequate penetration, and gas or slag inclusions. Among the weld defects that can be recognized visually are cracking, surface slag in inclusions, surface porosity and undercut.

Visual inspection can only locate defects in the weld surface. Specifications or applicable codes may require that welds be tested more thoroughly than a mere visual inspection.

X-ray Inspection

X-ray is one of the most important, versatile and widely accepted of all the nondestructive examination methods. X-ray may be used to determine the internal soundness of welds. X-ray testing is based on the ability of X-rays and gamma rays to pass through metal and other solid materials and produce photographic images of the transmitted radiant energy. All materials will absorb known amounts of this radiant energy and, therefore, X-rays and gamma rays can be used to show discontinuities and inclusions within the solid material.

X-rays or gamma rays are directed at a section of weld and only a portion of the rays pass entirely through the metal. Variations in the how the rays pass through and are recorded on a radiograph is indicative of variations within the metal. A material should absorb a certain amount of radiation, however, where the radiographs show less absorption, there may be a thin section or a void in the weld. The reliability and interpretive value of radiographs is a function of their sharpness and contrast.

Radiographs may be difficult to analyze. Filmhandling marks and streaks, fog and spots caused by developing errors may make it difficult to identify defects. Such film artifacts may mask weld discontinuities. Further, since surface defects show up on the film and may disguise defects and the angle of exposure also influences the image in the radiograph, it is difficult or impossible to evaluate fillet welds by this method.

Radiographic equipment produces radiation that can be harmful to body tissue in excessive amounts, so all safety precautions should be followed closely. All instructions should be followed carefully to achieve satisfactory results. Only personnel who are trained in radiation safety and qualified as industrial radiographers should be permitted to do radiographic testing.

Magnetic Particle Inspection

Magnetic particle inspection is a method of locating and defining discontinuities in magnetic materials. Magnetic particle inspection is excellent for detecting surface defects in welds, including surface cracks of all sizes in both the weld and adjacent base metal, subsurface cracks, incomplete fusion, undercut and inadequate penetration in the weld, as well as defects on the repaired edges of the base metal. In this method, probes are usually placed on each side of the area to be inspected, and a high amperage is passed through the workplace between them. A magnetic flux is produced at right angles to the flow of current. When the magnetic flux encounters a discontinuity, such as a longitudinal crack, they are diverted and leak through the surface, creating magnetic poles or points of attraction. A magnetic powder dusted onto the surface will cling to the leakage area more tenaciously than elsewhere, forming an indication of the discontinuity.

Although much simpler to use than radiographic inspection, the magnetic particle method is limited to use with ferromagnetic materials and cannot be used with austenitic steels. This method is best with elongated forms, such as cracks, and is limited to surface flaws and some subsurface flaws, mostly on thinner materials.

Dye Penetrant Inspection

Surface cracks and pinholes that are not visible to the naked eye can be located by dye penetrant inspection. It is widely used to locate leaks in welds and can be applied with austenitic steels and nonferrous materials where magnetic particle inspection would be useless.

Dye penetrant inspection is often referred to as an extension of the visual inspection method. In this method, a dye with good penetrating qualities is applied to the surface of the part to be examined. Capillary action draws the dye into the surface openings, and the excess present on the surface is then removed. A second developer is used to draw the dye from the cracks or pores to the surface. The presence of the dye indicates surface cracks or pores. The part to be inspected must be clean and dry, because any foreign matter could close the cracks or pinholes and exclude the dye. Dyes can be applied by dipping, spraying or brushing, but sufficient time must be allowed for the dye to be fully absorbed into the discontinuities. This may take an hour or more in very exacting work.

Ultrasonic Inspection

Ultrasonic Inspection is a method of detecting discontinuities by directing a high-frequency sound beam through the base plate and weld on a predictable path. When the sound wave encounters a defect in the material continuity, some of the sound is reflected back. The reflected waves are collected by the instrument, amplified and displayed as a vertical trace.

Both surface and subsurface defects in metals can be detected, located and measured by ultrasonic inspection, including flaws too small to be detected by other methods. The ultrasonic unit contains a crystal of quartz or other piezoelectric material encapsulated in a transducer or probe. When a voltage is applied, the crystal vibrates rapidly. As an ultrasonic transducer is held against the metal to be inspected, it imparts mechanical vibrations of the same frequency as the crystal through a coupler material into the base metal and weld. These vibrational waves are propagated through the material until they reach a discontinuity or change in density. At these points, some of the vibrational energy is reflected back. As the current that causes the vibration is shut off and on at 60-1000 times per second, the quartz crystal intermittently acts as a receiver to pick up the reflected vibrations. These cause pressure on the crystal and generate an electrical current. Fed to a video screen, this current produces vertical deflections on the horizontal base line. The resulting pattern on the face of the tube represents the reflected signal and the discontinuity. Compact portable ultrasonic equipment is available for field inspection and is commonly used on bridge and structural work.

Ultrasonic testing is less suitable than other NDE methods for determining porosity in welds, because round gas pores respond to ultrasonic tests as a series of single-point reflectors. This results in low-amplitude responses that are easily confused with "base line noise" inherent with testing parameters. Ultrasonic examination requires expert interpretation from highly skilled and extensively trained personnel.

In the art, the excitation and registration of the acoustic waves is performed by piezoelectric devices with inclined introduction emission. These systems do not allow for analysis to be carried out in a sufficiently wide band of ultrasonic frequencies and to ensure a sufficient locality of measurement of the stressed state of material and it is not possible to ensure both high accuracy and locality measurements needed in many measurement applications.

There exists a need for a nondestructive testing apparatus and method that is relatively inexpensive, accurate, and easy to use and easy to analyze the results.

SUMMARY

Embodiments of the nondestructive testing apparatus comprises a piezoelectric transducer for measuring oscillations in a solid, the oscillations may be caused from longitudinal, shear, and/or Raleigh waves in the object to be tested. The nondestructive testing apparatus may also comprise a laser. The laser is capable of generating longitudinal, shear, and/or Raleigh waves in the object. In certain embodiments, the nondestructive testing apparatus comprises a laser and a piezoelectric transducer.

One method of performing nondestructive testing of materials may comprise creating at least one of a longitudinal, shear, and/or Raleigh wave in an object and measuring the speed of the wave in the object. The speed of the waves may be compared with the speed of waves in a material without defects to determine whether the object to be tested has defects.

DESCRIPTION

Figure 1:
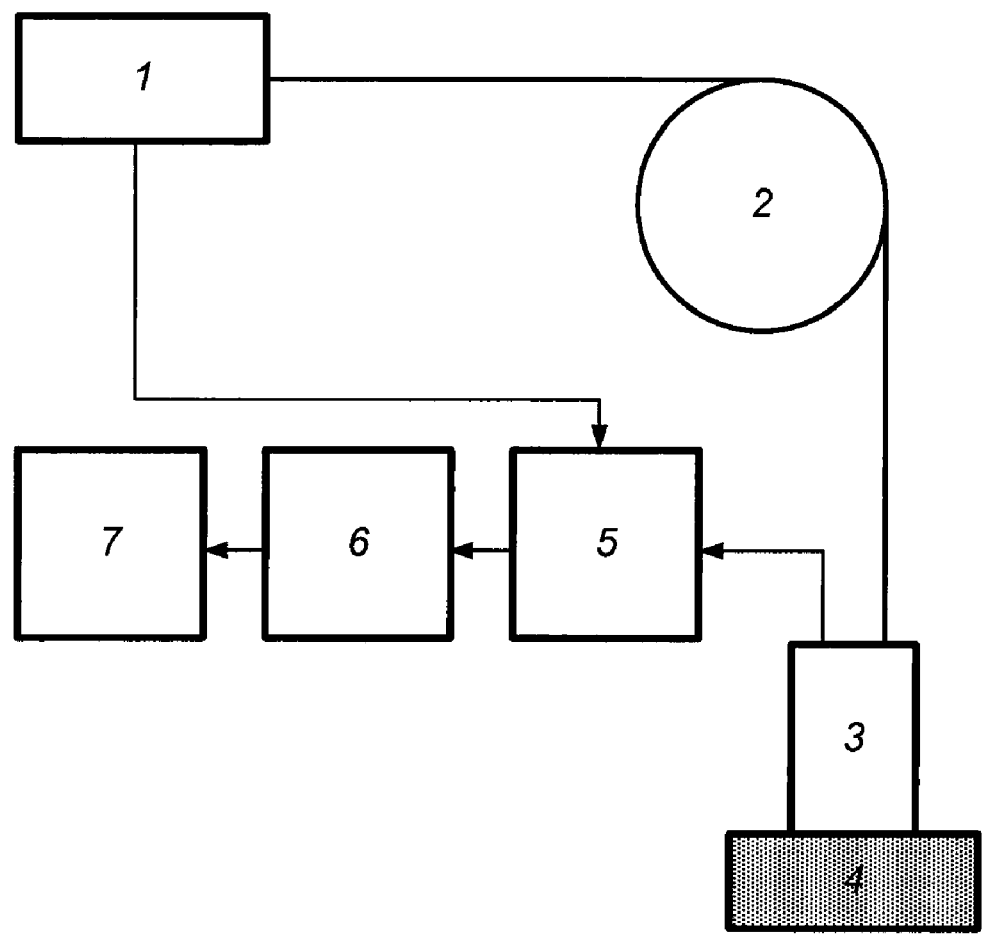
FIG. 1 is a block diagram showing the main components of an embodiment of the nondestructive testing apparatus.

Embodiments of the nondestructive apparatuses and methods provide accurate and reliable testing of materials. The testing may be conducted on any material including metals, carbon and stainless steels, aluminum, titanium alloys, nickel alloys, for example.

Embodiments of the nondestructive testing apparatus comprise a laser and a piezoelectric transducer. The nondestructive testing apparatus may comprise a pulsed laser in which radiation is focused on the surface of the object being investigated. The laser may be focused by optics into a point or a narrow strip on the surface of the object to be investigated. If focused on a narrow strip, the narrow strip may be linear or curved such as focused into a portion of a circle or an entire circle. The laser causes thermal expansion of the surface layer of the material which results in the formation of surface acoustic waves and internal waves in the material. The surface waves travel across the surface of the object and pass by the piezoelectric transducer. As the wave passes by the piezoelectric transducer, the transducer generates an electric signal that corresponds to the height of the wave.

In an embodiment of the nondestructive testing apparatus, both the optics and the piezoelectric transducer are both combined in a single unit or an optics-acoustic transducer. In such an embodiment, the optics may focus the laser pulse in a precise manner that is at a fixed distance from the detection point at which a portion of the piezoelectric transducer contacts the surface of the object. In an embodiment of the optic-acoustic transducer, the piezoelectric transducer is in dry acoustic contact with the surface of the object being investigated. The electrical signal produced by the piezoelectric is proportional to the normal vibrational velocity of the object and may be enhanced by an amplifier such as, but not limited to a broad band amplifier. The broad band amplifier may be directly integrated in the optic-acoustic transducer or integrated elsewhere in the circuitry of the apparatus. The pre-amplified or amplified signal may be converted into a digital signal for analysis and processing by a processing unit. The analog signal may be converted by, for example, a high-speed precision analog-digital converter. The digital signal may be filtered and mapped on a monitor, printout or other output device, if desired.

The degree of defects present in the system may be determined from the elapsed time from generation of the surface waves by the laser pulse to arrival of the surface waves at the detection point and generation of a signal by the piezoelectric transducer. The speed of the surface waves may be calculated if the distance between the location of the focused laser pulse on the surface and the contact point of the piezoelectric transducer is known. The wave velocity in a similar material in an area without stress may be compared to the wave velocity in an area with defects or residual stresses to determine the extent of the defects as residual stress. The differences in the surface wave velocities make it possible to determine the degree stress in the matter.

In embodiments, the nondestructive testing apparatus comprises an optical element. The beam of the laser may pass through the optical element to focus the beam in a desired pattern on the object to be tested. The optical element may be capable of focusing the laser in an elongated pattern. In embodiments of optical element that are capable of focusing the laser pulse into a strip, the strip may have a width between 0.01 mm and 1 mm and a length between 0.5 mm and 5 mm. In further embodiments, the strip may have a width between 0.1 mm and 1 mm and a length between 1 mm and 10 mm.

The optical element may preferably be a nonconducting optical element such as a crystal. The crystal may be a dielectric crystal, for example, such as but not limited to quartz and be a clear quartz crystal. In further embodiments, the optical element may comprise at least one compound selected from ethylene diamine tartrate, barium titanate, quartz, silicon dioxide, rochelle salt, potassium sodium tartrate, tourmaline, ammonium dihydrogen phosphate, ethylenediamine tartrate as well as other compounds with desirable optical qualities.

The laser must be capable of producing a surface wave on the object to be tested. The compromise can be achieved with application of wide-band ultrasonic pulses. Traditional piezoelectric techniques are not able to produce an ultrasound excitation in a wide frequency range. Ultrasonic transients excited by absorption of laser radiation in metals, however, follow the time envelop of the laser pulse intensity. This makes it possible to obtain nanosecond ultrasonic pulses with an aperiodic temporal profile and the wide frequency spectrum and pressure amplitudes being up to a few hundreds of MPa. Thus, the size of the surface wave depends on the duration and power of the laser pulse. In certain embodiments, the laser may be a constant source of a light beam but the optics may be capable of producing a short laser pulse to contact the surface of the object to be tested. In specific embodiments, the laser or optics may be capable of producing a laser pulse of one nanosecond to 20 nanoseconds or even a laser pulse of 5 nanoseconds to 10 nanoseconds. Further, the laser may be capable of producing a laser pulse at a power sufficient to create a surface wave. For example, the laser may have a power level from 30 µJ to 500 µJ or for certain applications the laser is capable of producing a laser pulse at a power level from 50 µJ to 250 µJ. The laser may be used to generate longitudinal, shear, and/or Raleigh waves in the object to be tested.

Specific embodiments of the nondestructive testing apparatus comprise a laser and an optico-acoustic transducer. Such embodiments of the nondestructive testing apparatus may further comprise a fiber optic cable, wherein the laser light pulse travels from the laser through the fiber optic cable to the optico-acoustic transducer. The optico-acoustic transducer further comprises the piezoelectric transducer capable of generating an electric signal in response to oscillations or waves. The nondestructive testing apparatus may further comprise a piezoelectric signal processor, wherein the piezoelectric signal processor is in electrical communication with the piezoelectric transducer. In a typical embodiment, the piezoelectric signal processor may include any of the following components: an amplifier, an analog to digital converter, a signal filter, a computer, an output device as well as other components or software for processing an electric signal from the piezoelectric transducer.

Further embodiments of the optico-acoustic transducer may comprise a piezo-electric transducer and an optical element. The optical element is capable of focusing a laser beam or laser pulse. The optico-acoustic transducer may further comprise a fiber optic cable.

As described above, surface waves created by the laser and/or optics on the surface of the object travel through the object to be received and converted to electricity by the piezoelectric transducer. The piezoelectric transducer must be capable of sensing the surface waves or oscillations and therefore, comprises a material contacting member. In specific embodiments, the material contacting member is adapted to provide a small contact surface. A small contact surface allows a more accurate reading of the surface waves or oscillations since the wave passes the material contacting member in the shortest time. In certain embodiments, the small contact surface may be a portion of a sphere, for example, a spherical sound duct. The small contact surface may be substantially a point contact surface.

The optico-acoustic transducer has a measurement end that is adapted to contact the surface of the object to be tested. In a preferred embodiment, the measurement end has three feet for contacting the object to be tested. In such an embodiment, the material contacting member is biased toward the measurement end and/or the object to be tested. The material contacting member may be biased toward the material contacting end and/or the object to be tested by a spring. In certain applications, the spring has a normalized strength of pressing.

Nondestructive testing of materials by ultrasonic methods can be used to identify residual stresses in the subsurface state of the materials. In this embodiment, the nondestructive testing apparatus and method is based on acousto-elastic effect of the impact velocity dependence of surface acoustic waves on the subsurface stresses. The methods may comprise excitation of planar beams of surface ultrasonic waves using a pulsed laser and registration of surface acoustic waves by a piezoelectric transducer. In some cases, the piezoelectric transducer may comprise a high temporal resolution.

Such apparatuses and methods provide a reliable method of nondestructive inspection of the stressed state of solid materials. In certain embodiments of the method laser excitation of broad band ultrasonic pulses at the surface of the material and the registration of the imparted pulses at a certain distance from the site of excitation by a mechanical contact of piezoelectric element with the surface of the object to be tested.

EXAMPLE

A block diagram showing the main components of an embodiment of a nondestructive testing apparatus is shown in FIG. 1. The embodiment of FIG. 1 is for the laser-acoustic testing of the stressed state of solid materials. The theory of operation disclosed herein is provided merely to describe the present understanding of the operation of the apparatus and not to limit the scope of the apparatus or method.

In the embodiment of the nondestructive testing apparatus of FIG. 1, Laser 1 produces laser pulses. The laser pulses pass through an optical fiber cable 2 to optico-acoustic transducer 3. An embodiment of the optico-acoustic tranducer 3 is shown in more detail in FIG. 2. The optico-acoustic transducer 3 is in contact with an object 4 to be tested. Optics in the optico-acoustic transducer 3 focus the laser pulse into a narrow strip on the surface of object 4. The laser pulse radiation is absorbed on the surface of the object 4, a surface acoustic wave is generated due to rapid thermal expansion on a localized portion of the object 4. The wave propagates through and along the surface of the object 4. As discussed previously, the propagation velocity of the surface acoustic wave depends on, among other things, the mechanical stress present in the surface layer of the object 4, where acoustic oscillations propagate. The acoustic oscillations at the surface are detected by the piezoelectric transducer, see FIG. 3, within the optico-acoustic transducer 3 which is in a dry point contact with a medium under investigation. The optico-acoustic transducer is pressed to the surface of the medium. The piezoelectric transducer converts the oscillations in the surface layer into an electrical signal. The electrical signal is substantially proportional to the particle velocity of the surface and is digitized by an analog-to-digital converter 5, band-pass filtered in signal filter 6, and displayed on an output device 7. The propagation velocity of the surface acoustic wave is determined by calculating the duration of time between generation of the wave and arrival of the signal peak of a surface wave at the detection point of the piezoelectric transducer and the distance between the laser excitation site and the contact point of the piezoelectric transducer.

In the embodiment shown in FIG. 1, the nondestructive testing apparatus includes a computer configured to calculate the propagation velocity of the surface acoustic wave. The computer includes memory, a processing unit, an input device and software or hardware capable of making the calculations and producing an output. In such an embodiment, an electrical signal synchronized with the laser pulse triggers the reading process in analog-to-digital converter 5. The measured propagation velocity is compared to the propagation velocity of a surface acoustic wave in the reference region where stress is absent or based upon a value in a database to determine the amount of mechanical stress in the subsurface region of the object 4.

Figure 2:
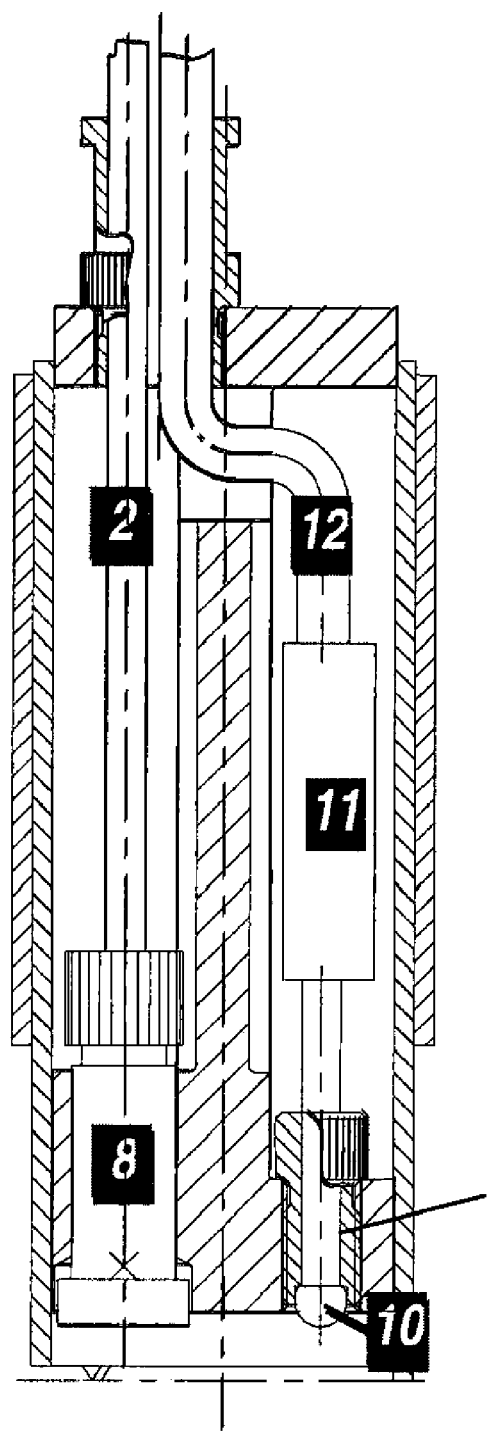
FIG. 2 is a design layout for an embodiment of the optico-acoustic transducer.
Figure 3:
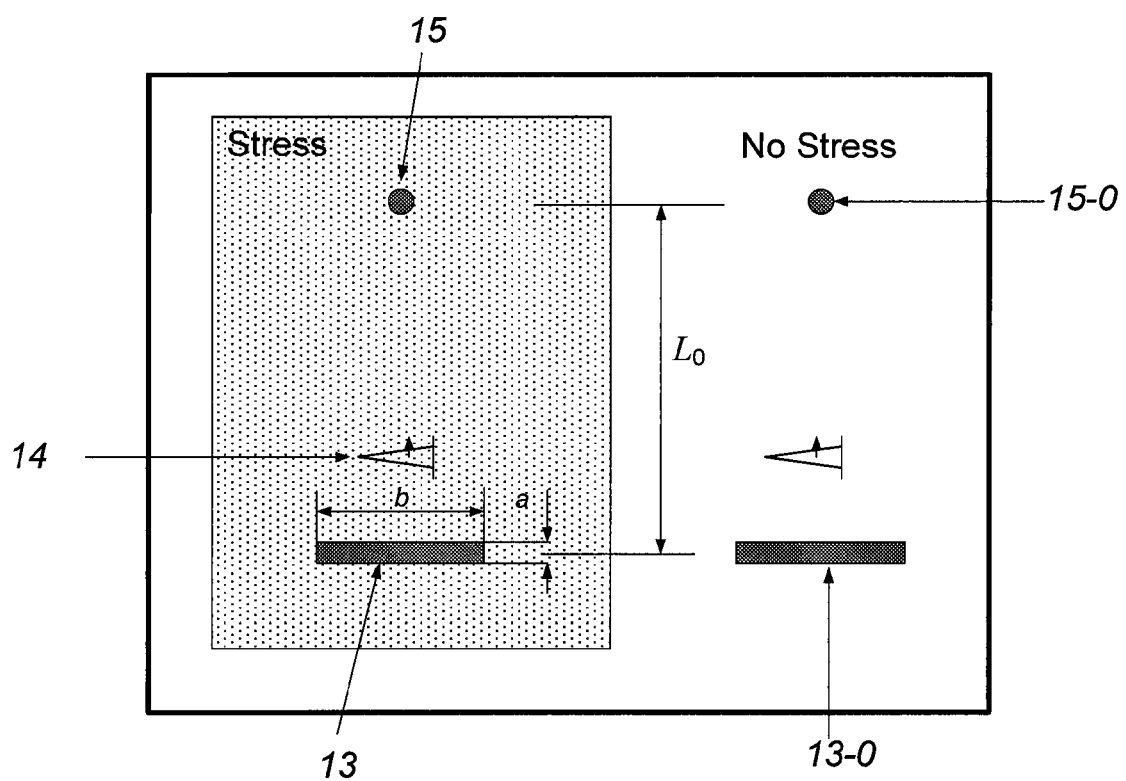
FIG. 3 is a graphical representation showing the relative positions of the focused laser radiation strip and the pressing point of the surface contacting member of piezoelectric transducer on the surface of the object to be tested.

An embodiment of an optico-acoustic transducer is shown in FIG. 2. The optical fiber cable 2 is connected to optics 8 capable of focusing a laser pulse into a narrow strip or other pattern on the surface of the object under investigation. The thickness "a" of the strip 13, see FIG. 3, determines the length of an excited pulse of surface acoustic waves 14 and the width "b" of the strip 13 contributes to the directionality of the radiated beam of surface acoustic waves. Surface oscillations are detected by the piezoelectric transducer with a spherical sound duct 10, which is pressed to the investigated surface by a spring (not shown).

An electrical signal from the piezoelectric transducer that is proportional to the particle velocity of the surface is amplified by a wideband charge preamplifier 11 and transmitted through an electrical cable 12 to the analog to digital converter 5. A method of measuring the stressed state of an object may be better understood with reference to FIG. 3. A portion of the object 8 under the optico-acoustic transducer is shown. Laser radiation is focused by the optical system (see FIG. 2) into a narrow strip 13 in the region under investigation. The narrow strip has a length "b" and a width "a". An excited pulse 14 of a surface acoustic wave propagates along the surface under investigation to the detection point 15. The excited pulse travels a distance $L_0$ and the arrival time at detection point 15 is determined by the analysis of the output of the piezoelectric transducer. The velocity of a surface acoustic wave in the region under investigation is determined by Eq. (2).

$$c_R = \frac{L_0}{\Delta t - \Delta t_0} \quad (2)$$

Here $L_0$ Distance traveled by a surface acoustic wave from a point to the detection point and $\Delta t_0$ is the time of signal delay in the piezoelectric transducer.

Residual stresses state in welds lie on the level of the yield point, which is amounted 600 MPa. The relative deviations of longitudinal wave velocities is directly proportional to stress:

$$\frac{\Delta V}{V} = A \cdot \sigma.$$

The coefficient A can be calculated from the second and third order elastic constants of the material. A typical value for A is approximately $10^{-12} \, Pa^{-1}$, therefore the maximum of the ratio of $$\frac{\Delta V}{V} \approx 10^{-3},$$

that introduces the additional time delay of the order of only a few nanoseconds for the thickness of a sample of 1 cm. Thus time intervals between signals would be measured better then 1 ns.

The optico-acoustic transducer may be moved to a stress-free surface region to determine the velocity of a surface acoustic wave in a stress free condition. The analysis is repeated by focusing the laser on location 13-0 and measuring the arrival time of the pulse of the surface acoustic wave at detection point 15-0. The stress states in the surface region under investigation are determined by Eq. (1).

Figure 4:
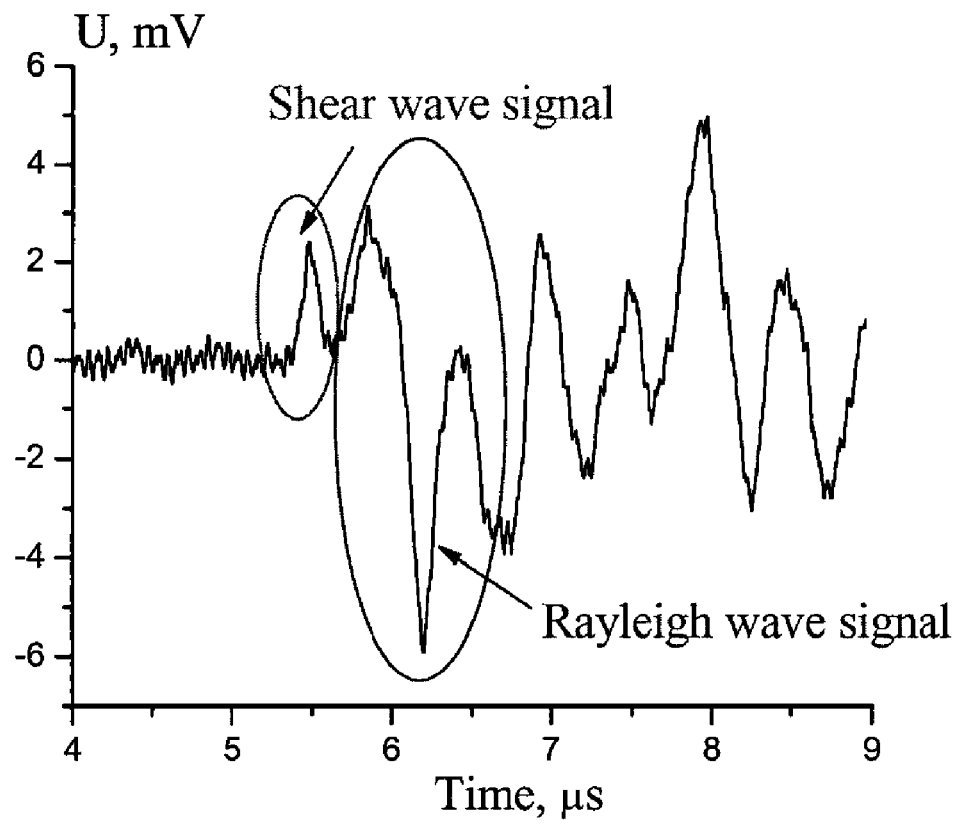
FIG. 4 is a graphical representation of the surface acoustic waves and illustrates a method for determination of the arrival time for a surface acoustic wave.

A method of determining the arrival time for a pulse of a surface acoustic wave is illustrated in FIG. 4. FIG. 4. illustrates a graph of a signal track from a piezoelectric transducer as described above after the signal is filtered. The arrival time of a pulse of a surface acoustic wave of the detection point is the moment of the rise of a signal extremum from a surface acoustic wave (the minimum in this case indicated by an arrow). The delay of the extremum arrival may be accounted for and the velocity of a surface acoustic wave is calculated by Eq. (2). The values of $L_0$ and $\Delta t_0$ are determined by the design of the optico-acoustic transducer and are its defined characteristics.

Thus the proposed technique for laser-acoustic monitoring of stressed states of solid materials and the device for its implementation have higher accuracy and repeatability of measurements in comparison with a other methods. In this embodiment, the use of an optico-acoustic transducer integrating excitation point and piezodetection point of a surface acoustic wave in one unit, the optico-acoustic transducer, provides an opportunity to increase the system sensitivity and reduce the requirements to the surface quality for a sample under investigation.

An embodiment of the optico-acoustic transducer comprises an optical system and a piezoelectric sensor that is connected in series with an amplifier, filter, and signal registration device; the optical system and the piezoelectric sensor are unified into a single functional module. In such an embodiment, the laser beam may be focused into a narrow strip at a fixed distance from the detection point of the piezoelectric transducer on the surface of the object under investigation. The integrated optico-acoustic transducer is capable of radiating and detecting acoustic pulses to accurately determine the velocity of the wave since the distance between the detection point and the generation point is fixed. The spring provides a constant and consistent pressing of the optico-acoustic transducer to the surface thereby improving the repeatability of measurements.

Further, the electric signal from a piezosensor may be amplified by a wideband charge preamplifier and digitized. After corresponding frequency filtering the delay time for the arrival of the peak of a surface wave pulse is determined with respect to a laser pulse. The local propagation velocity of a surface acoustic wave in the material under investigation is determined according to it. To eliminate the effect of texture and temperature, the propagation velocity of a surface acoustic wave in an approximate parallel direction is measured in the region of the medium under investigation, where stress is absent. The relative variations of the velocity in these two regions determine the local subsurface stress, $$\sigma \sim c_R - c_{R0}, \tag{1}$$

where $c_R$, $c_{R0}$ are the velocities of a surface acoustic wave in the investigated surface region with stress and in the reference region without stress, respectively. To determine the absolute value of stress it is necessary to know the proportionality factor that may be determined separately in the process of calibration. Proportionality factors of specific materials may be stored in a data base in the processing unit.

Wide-band laser excited nanosecond ultrasonic waves were used to determine relative deviations of phase velocities of ultrasound with the accuracy being suitable for reconstruction of residual stresses in welds. An optico-acoustic transducer operated in backward mode and combining into one both the optical scheme for the excitation of the probe ultrasonic pulses on the surface of welded samples under study and the wide-band piezodetection with a high temporal resolution had been developed. Samples of stainless steel with the thickness of from 1.67 mm to 8.97 mm welded over their center by the electronic beam of different intensities were studied with the developed technique.

Figure 5:
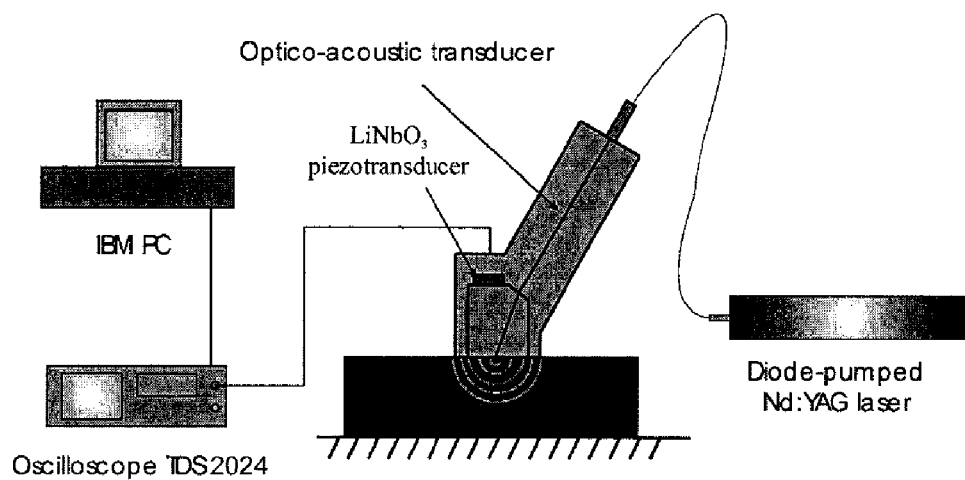
FIG. 5 is an embodiment of the nondestructive testing apparatus.

The nondestructive testing apparatus comprised a diode pumped Nd:YAG laser operating at the fundamental mode (the pulse energy ~100 μJ, the time duration of 7 ns) for irradiating metal samples. Laser radiation was delivered to the optico-acoustic transducer, see FIG. 5, where it was focused onto the front surface of a sample.

The diameter of the probe acoustic beam was equal to the laser beam, 4 mm. The laser pulse is absorbed in the skin layer of metal to a depth on the order of 10-6 cm. Due to the nonstationary heating and subsequent thermal expansion, excitation of ultrasonic transients, optico-acoustic pulses, are created in the metal. Optico-acoustic pulses travel in opposite directions from the excitation point. The first signal—the probe pulse—propagates through the clear quartz prism and is detected by wide-band piezoelectric transducer. The second one propagates into a sample, reflected from its rear surface and then is detected in a similar manner. Time delay between the probe optico-acoustic pulse and the pulse reflected from the rear surface is determined.

Figure 6:
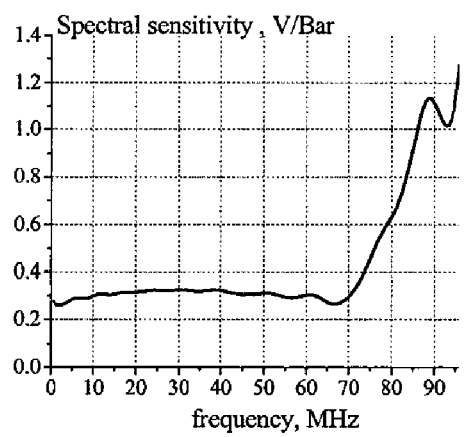
FIG. 6 is a graph showing the spectral sensitivity of wide band piezoelectric transducer.

If a sample has a thickness less than 5 mm, a multipass method was used. A wide-band piezoelectric transducer was operated in the open-circuit regime (lower half-wave resonance). In this embodiment, the nondestructive testing apparatus comprised a niobate-lithium piezoelement having a thickness of approximately 130 μm. The spectral sensitivity of the transducer is shown in FIG. 6. As can be seen, in the frequency range up to 70 MHz this function is close to a constant.

The output device was a digital oscilloscope Tektronix TDS 2024 for registration of ultrasonic data. A personal computer was used to record and process the data.

Samples

Figure 7:
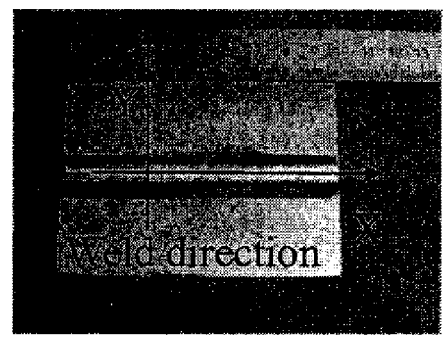
FIG. 7 show a test sample with a layout of the coordinate system used to describe the test locations in the sample, where the X-axis is along the weld and the Y-axis is generally perpendicular to the weld.

Samples of stainless steel with the thickness of from 1.67 mm to 8.97 mm welded over their center by the electronic beam of different intensities were studied with the developed method. A photo of one of samples under study and the coordinate system attached with it are shown of FIG. 7. The dimensions of each of the samples are listed in Table 1. Before measurements surfaces of welded samples were polished to be plane-parallel. Thicknesses of samples were measured by the micrometer with the inaccuracy of 2 μm in each point, where the velocity of ultrasound had been measured.

TABLE 1

Types of samples

| Type of the sample | Dimensions L × W × H, mm | Width of the weld area, mm | Power of the electronic beam, W |
| --- | --- | --- | --- |
| A-1 | 106.5 × 78 × 8.51 | 5 | 3200 |
| A-2 | 106.5 × 78 × 8.87 | 6 | 3200 |
| A-3 | 106.5 × 78 × 8.73 | 7 | 3200 |
| C-1 | 80 × 50 × 1.91 | 2 | 800 |
| C-2 | 80 × 50 × 1.67 | 3 | 800 |
| C-3 | 80 × 50 × 1.97 | 4 | 800 |

Time-of-flight measurements of relative deviations of phase velocities of longitudinal ultrasonic waves were carried out. First, the ultrasound velocity was measured in the reference samples of each group in an unwelded portion. Then measurements were made in the welded portion of the samples. In both cases the phase velocities were determined by the same scheme.

Figure 8:
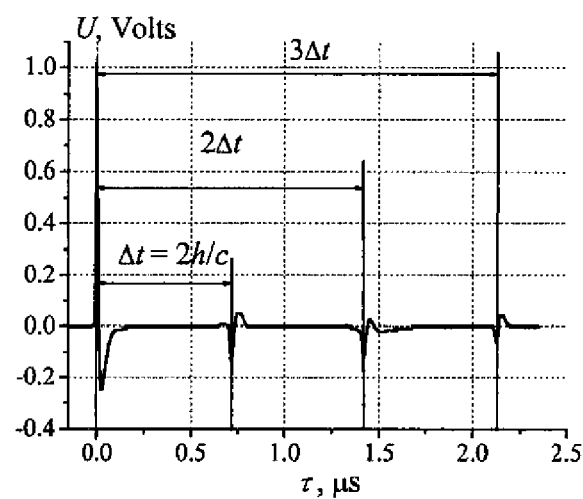
FIG. 8 is a graph of the oscillations recorded by an optico-acoustic transducer in a welded sample.

FIG. 8 shows a typical process of reverberations of ultrasonic pulses in a sample. The first pulse (see FIG. 9) is the probe ultrasonic signal. It is excited on the front surface of a sample under study by opto-acoustic transformation. As it follows from the theory of the opto-acoustic phenomenon, the temporal profile of the laser excited ultrasonic transient in metals should repeats the time envelop of laser pulse intensity, which can be described by the Gaussian function. Definite differences of the probe pulse temporal profile from Gaussian form are explained by both the diffraction of ultrasound in the acoustic line of the transducer and non-uniformity of the spectral sensitivity of the transducer on high frequencies.

Figure 10:
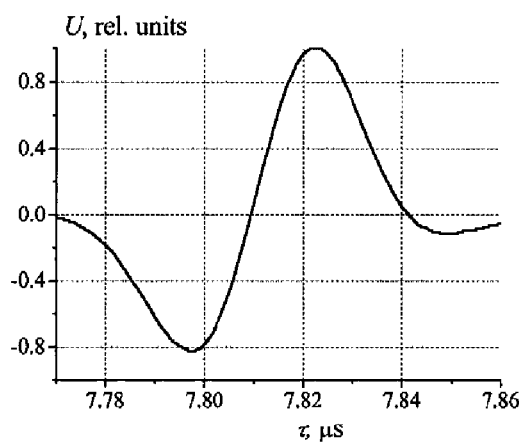
FIG. 10 is a graph of an echo signal of a pulse as detected by the piezoelectric transducer of an embodiment of the optico-acoustic transducer.

Echo signals reflected from the rear surface of a sample (see FIG. 10) come after the probe ultrasonic pulse in the equidistant intervals, which are the time of the ultrasonic wave double flight over a sample. A typical temporal profile of the echo signal is shown in FIG. 10. It is close to a bipolar form due to the attenuation and diffraction of ultrasonic waves during their propagation in a metal. The time-delay between probe and echo signals determines the sound velocity, which, as it was noted above, should be measured very precisely. In this embodiment of the nondestructive testing method, a time-delay between any signals can be measured with the accuracy of 0.5 ns. Therefore, to achieve the desired accuracy, the second or even third echo pulse detected was used in the calculation to increase the acoustical path length if the samples had the thickness less than 5 mm.

The arrival time of the probe pulse on the piezoelectric transducer is characterized by the point of the maximum of this signal, whereas the temporal profile of the echo pulse is differentiating during its propagation through the sample due to diffraction. Therefore the zero point of an echo pulse corresponds to its arrival time. The time delay between the specific points of these pulses allows one to determine the group velocity of ultrasound in welded samples. However the group velocities enable to reconstruct the residual stress state only in the case of its coincidence with phase velocity. This case takes place only when propagation of acoustic waves in a medium occurs without frequency dispersion.

It is more accurate to use the phase velocities for the reconstruction of residual stresses. The time delay between ultrasonic signals should be calculated with the phase-frequency spectra of these signals:

$$\Delta t = \frac{\Delta \varphi}{2\pi f} = \frac{\varphi_{probe} - \varphi_{echo}}{2\pi f} = \frac{tg\alpha}{2\pi}. \quad (26)$$

Here $\phi_{probe}$ and $\phi_{echo}$ are spectral phases of the probe and echo signals, f—a frequency, $\alpha$—the slope angle of the function $\Delta\phi(f)$. The wide frequency band of OA signals enables to calculate the value of $\alpha$ with very high accuracy by fitting the dependency of $\Delta\phi(f)$ with a line function in the frequency range, where the diffraction and attenuation of ultrasound are negligible. The inaccuracy of $\Delta t$ calculation with such procedure didn't excide 0.5 ns.

The phase velocities of longitudinal acoustic waves in reference samples without weld are measured firstly by the method described above. The obtained values of phase velocities for the samples of A and c groups were $V_{l0A}$=5657±2 m/s and $V_{l0C}$=5752±3 m/s, respectively. For determination of the spatial distribution of residual stresses the phase velocities of ultrasound were measured at 120-150 points of each sample. Measurements were carried out in 10 mm step one from another along the X-axis, and in 2 mm increments near the weld and in 5 mm steps away from the weld along the Y-axis. Incremental steps were chosen because the residual stress distribution is steeper near the weld and relatively smooth along the weld direction and far of the weld. Measurements were repeated at each point and the average value and correlation were calculated and graphed. Since the diameter of probe acoustic beam was 4 mm, readings near the weld were averaged over three points.

Figure 11A:
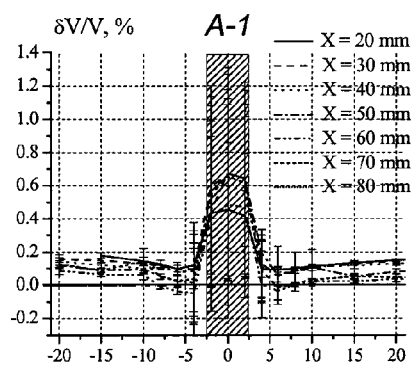
FIGS. 11A-11C are graphs showing the dependency of the relative deviations of velocities of longitudinal ultrasonic waves vs. coordinate Y across the weld at the different values of coordinate X along the weld for samples of the group A.
Figure 12A:
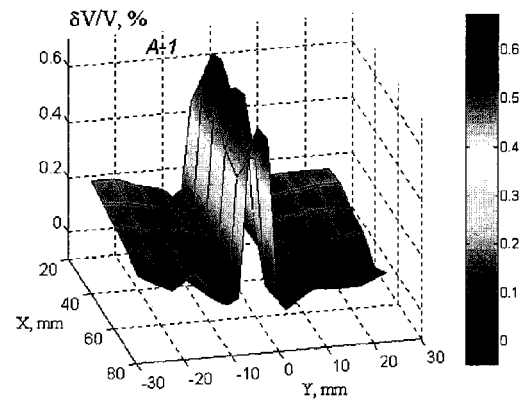
FIGS. 12A-12C are graphs of three dimensional surfaces of the distribution of relative deviations of velocities of longitudinal ultrasonic waves for samples of the group A.
Figure 11B:
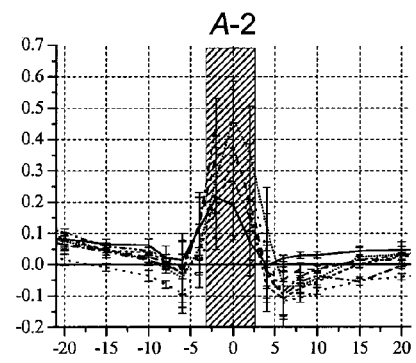
Figure 12B:
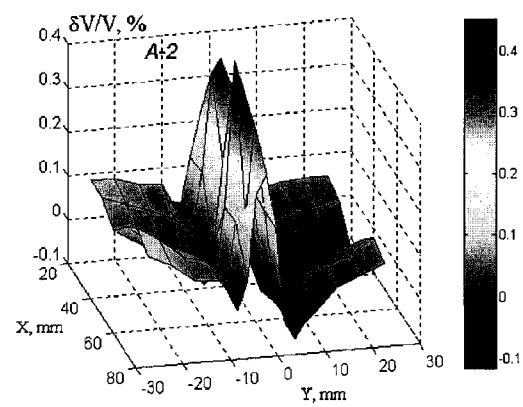
Figure 11C:
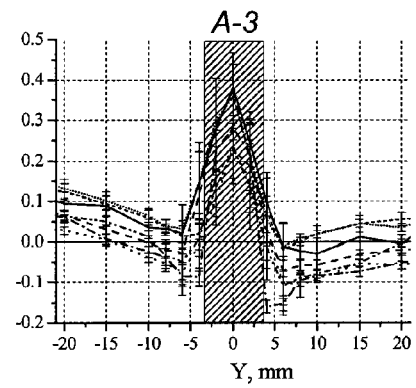
Figure 12C:
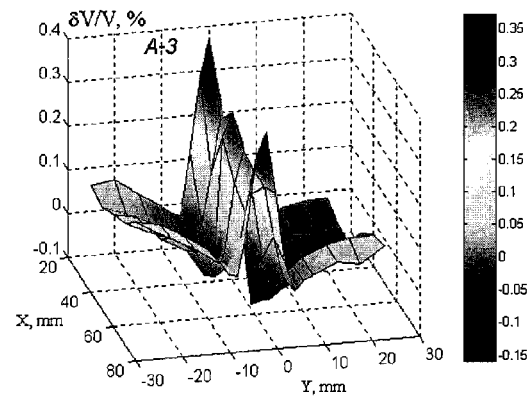
Figure 13A:
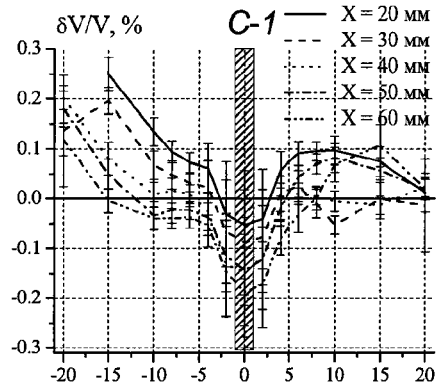
FIG. 13A-13C are graphs showing the dependency of the relative deviations of velocities of longitudinal ultrasonic waves vs. coordinate Y across the weld at the different values of coordinate X along the weld for samples of the group C.
Figure 14A:
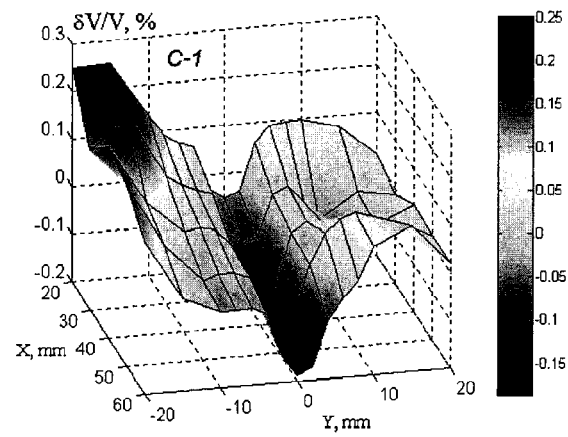
FIG. 14A-14C are graphs of three dimensional surfaces of the distribution of relative deviations of velocities of longitudinal ultrasonic waves for samples of the group C.
Figure 13B:
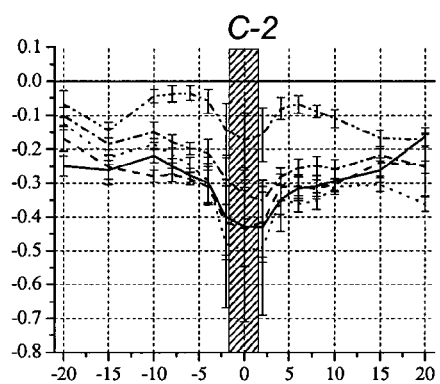
Figure 14B:
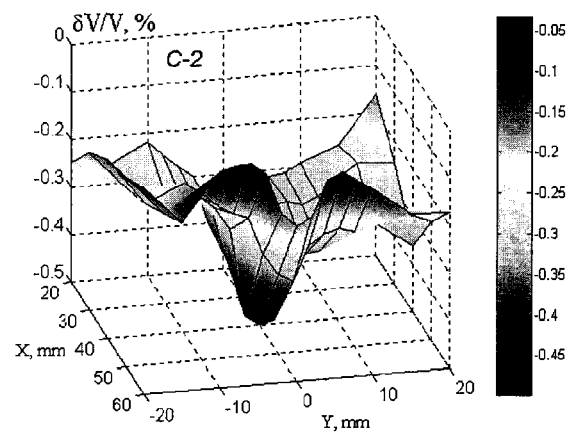
Figure 13C:
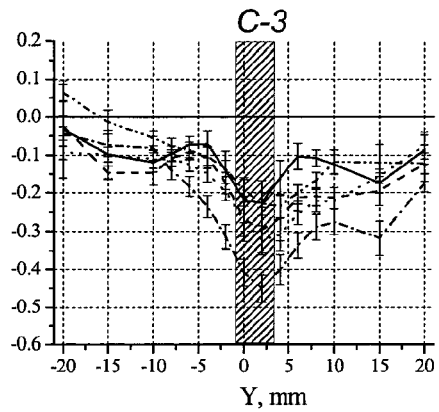
Figure 14C:
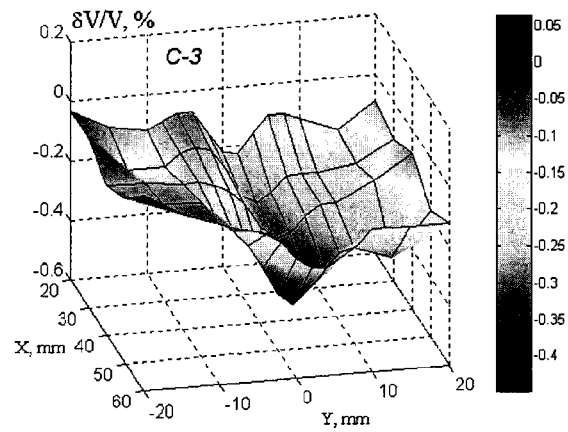

FIGS. 11A-11C represent experimentally obtained distribution of relative deviations of the phase velocity of ultrasound for the samples of the group C. The crosshatched region correspond to the welding area. 3-D surfaces of the residual stress distribution built with respect of the data represented in FIG. 11A-11C are shown in FIG. 12A-12C. FIGS. 13A-13C and 14A-14C represent the distribution of residual stresses for the samples of the group.

Figure 9:
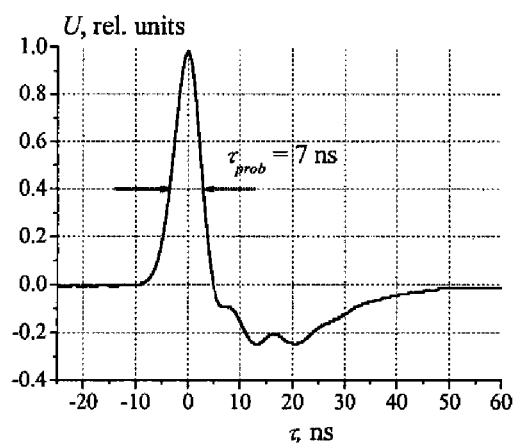
FIG. 9 is a graph of a typical reading of a pulse as detected by the piezoelectric transducer of an embodiment of the optico-acoustic transducer.

FIGS. 8 and 9 demonstrate that tensile stresses are presented in the weld area in "thick" samples, nearby the weld residual stresses change the sign and turn into compressing ones. Tensile stresses appear once again far of the weld. This tendency is explained by the process of welding. Indeed, welding is accompanied with nonuniform thermal heating of a material. Subsequent cooling leads to volume decreasing of contiguous layers of a metal, producing by this way the compressing stress. We can see in FIG. 9 also that the dependencies of $\delta V/V$ "go down" from the one edge of the samples (X=20 mm) to the center (X=50-60 mm) and then "go up" to another edge (X=80 mm). It means that not only longitudinal stresses $\sigma_{22}$ are presented in these samples as well as transversal stresses take place too. The compressing stress area is changed depending on both the intensity of the electron beam and its width: the sample A-3 has the widest compression zone, A-3 it is the most of narrow.

The special distribution of residual stresses for the samples of group C is similar with the group A as seen in FIGS. 13A-13C and FIGS. 14A-14C. The compressing stress area is changed depending on the regime of welding, but compressing stresses prevail over tensile ones. It may be explained by heating-through of the "thin" samples leading to subsequent partial in-depth relaxation of the tensile stress state.

While the invention has been disclosed in specific embodiments, it will be apparent to those skilled in the art that many modifications, additions, and deletions can be made therein without departing from the spirit and scope of the invention and its equivalents as set forth in the following claims.

The invention claimed is:

1. An apparatus for measuring stress in a material, comprising
    a laser; and
    an optico-acoustic transducer, wherein the optico-acoustic transducer comprises an optical element and a piezoelectric transducer and a beam from the laser passes through the optical element.

2. The apparatus of claim 1, wherein the piezoelectric transducer is connected to a material contacting member.

3. The apparatus of claim 2, wherein the material contacting member is adapted to provide a small contact surface.

4. The apparatus of claim 3, wherein the small contact surface is a portion of a spherical sound duct.

5. The apparatus of claim 3, wherein the small contact surface is substantially a point contact surface.

6. The apparatus of claim 5, wherein the optico-acoustic transducer has a measurement end and the material contacting member is biased toward the measurement end.

7. The apparatus of claim 6, wherein the material contacting member is biased by a spring.

8. The apparatus of claim 7, wherein the spring has a normalized strength of pressing.

9. An apparatus for measuring stress in a material, comprising:
    a laser;
    an optico-acoustic transducer optically connected to the laser by a fiber optic cable, wherein the optico-acoustic transducer comprising:
        an optical element capable of focusing the laser in a narrow strip on the surface of an object for creating a surface acoustic wave; and a piezoelectric transducer for measuring the surface acoustic wave, wherein a spring biases the piezoelectric transducer toward a measurement end of the optico-acoustic transducer; and a computer configured to calculate a propagation velocity of the surface acoustic wave.

10. The apparatus of claim 9, wherein the narrow strip has a width between 0.01 mm and 1 mm and a length between 0.5 mm and 5 mm.

11. The apparatus of claim 9, wherein the strip has a width between 0.1 mm and 1 mm and a length between 1 mm and 10 mm.

12. The apparatus of claim 9, wherein the optical element is one of a nonconducting optical element, a crystal, a dielectric crystal, clear quartz, or a clear quartz prism.

13. The apparatus of claim 12, wherein the optical element comprises at least one compound selected from ethylene diamine tartrate, barium titanate, quartz, silicon dioxide, rochelle salt, potassium sodium tartrate, tourmaline, ammonium dihydrogen phosphate, and ethylenediamine tartrate.

14. The apparatus of claim 9, wherein the laser is capable of producing a laser pulse.

15. The apparatus of claim 14, wherein the laser is capable of producing a laser pulse of one nanosecond to 20 nanoseconds.

16. The apparatus of claim 15, wherein the laser is capable of producing a laser pulse at a power level from 30 µJ to 500 µJ.

* * * * *